(12) United States Patent
Sim et al.

(10) Patent No.: US 10,458,911 B2
(45) Date of Patent: Oct. 29, 2019

(54) METHOD FOR SEARCHING CANDIDATE MATERIAL FOR ANTI-CANCER DRUG USING LOCALIZED SURFACE PLASMON RESONANCE

(71) Applicant: KOREA UNIVERSITY RESEARCH AND BUSINESS FOUNDATION, Seoul (KR)

(72) Inventors: Sang Jun Sim, Seoul (KR); So Jin Song, Seoul (KR)

(73) Assignee: KOREA UNIVERSITY RESEARCH AND BUSINESS FOUNDATION, Seoul (KR)

(*) Notice: Subject to any disclaimer, the term of this patent is extended or adjusted under 35 U.S.C. 154(b) by 517 days.

(21) Appl. No.: 15/141,196

(22) Filed: Apr. 28, 2016

(65) Prior Publication Data

US 2016/0363583 A1 Dec. 15, 2016

(30) Foreign Application Priority Data

Apr. 28, 2015 (KR) .................. 10-2015-0059720
Apr. 11, 2016 (KR) .................. 10-2016-0044107

(51) Int. Cl.
| | | |
|---|---|---|
| *G01N 33/553* | (2006.01) | |
| *G01N 21/47* | (2006.01) | |
| *G01N 33/543* | (2006.01) | |
| *G01N 21/552* | (2014.01) | |

(52) U.S. Cl.
CPC ............ *G01N 21/47* (2013.01); *G01N 21/554* (2013.01); *G01N 33/54346* (2013.01); *G01N 33/553* (2013.01); *G01N 2333/47* (2013.01)

(58) Field of Classification Search
None
See application file for complete search history.

(56) References Cited

U.S. PATENT DOCUMENTS

| | | | | |
|---|---|---|---|---|
| 2008/0076676 A1* | 3/2008 | Kim | ..................... | B82Y 15/00 506/12 |
| 2012/0184451 A1* | 7/2012 | Singamaneni | ........... | B82Y 5/00 506/9 |
| 2015/0065688 A1* | 3/2015 | Ragan | .................... | B01J 20/289 530/367 |
| 2015/0204865 A1* | 7/2015 | Lin | ...................... | G01N 33/553 436/501 |

FOREIGN PATENT DOCUMENTS

| | | |
|---|---|---|
| KR | 10-2007-0114660 A | 12/2007 |
| KR | 10-2010-0082126 A | 7/2010 |

OTHER PUBLICATIONS

Yue et al, "Targeting STAT3 in cancer: how successful are we?", Expert Opin. Investig Drugs, Jan. 2009; 18(1); 45-56.*
Jinbo Yang et al., "Unphosphorylated STAT3 Accumulates in Response to IL-6 and Activates Transcription by Binding to NFκB", Genes & Development, 2007, pp. 1396-1408 and cover page.
Yun et al., "Positively-charged Gold Nanoparticles as Peroxidiase Mimic and Their Application in Hydrogen Peroxide and Glucose Detection", Chem. Commun., 2010, 46, pp. 8017-8019.
Ken Miyoshi et al., "Stat3 as a Therapeutic Target for the Treatment of Psoriasis: A Clinical Feasibility Study with STA-21, a Stat3 Inhibitor", Journal of Investigative Dormotology (2011), vol. 131, pp. 108-117.

\* cited by examiner

*Primary Examiner* — Christopher L Chin
(74) *Attorney, Agent, or Firm* — Oblon, McClelland, Maier & Neustadt, L.L.P.

(57) ABSTRACT

A method for screening an anticancer candidate is disclosed. The method includes immobilizing gold nanoparticles onto a substrate; binding a protein involved in carcinogenesis and metastasis to the immobilized gold nanoparticles, recording a spectrum of the protein conjugate, and analyzing the spectrum to obtain reference data; adding a candidate inhibiting the activity of the protein to the protein conjugate, recording a spectrum of the mixture, and analyzing the spectrum to obtain comparative data; and comparing the reference data with the comparative data to determine whether the candidate inhibits the activity of the protein. The method enables screening of a candidate inhibiting the activity of a protein involved in carcinogenesis and metastasis in an accurate and convenient manner.

5 Claims, 15 Drawing Sheets

METHOD FOR SEARCHING CANDIDATE MATERIAL FOR ANTI-CANCER DRUG USING LOCALIZED SURFACE PLASMON RESONANCE

BACKGROUND OF THE INVENTION

1. Field of the Invention

The present invention relates to a method for screening an anticancer candidate.

2. Description of the Related Art

Localized surface plasmon resonance (LSPR) has been used extensively in a number of studies on interactions between surface-immobilized biomolecules due to its ability to quantitatively detect reactions without the need for complicated preliminary purification and labeling steps. According to LSPR, when light of various wavelengths is irradiated onto metal nanoparticles as surface-localized materials, polarization occurs on the surface of the metal nanoparticles and is responsible for their unique properties, such as enhanced electric field intensity. This physical phenomenon does not occur in a bulk metal. The optical properties of LSPR respond sensitively to changes in the dielectric constant (refractive index) near the surface of nanoparticles, allowing such dielectric constant (refractive index) changes to be used to detect adsorption between biomolecules.

STAT3 protein is a transcriptional regulatory factor involved in the transcription of several genes in human cells. In normal cases, STAT3 present in the cytoplasm translocates into the nucleus and regulates genes for cell development, differentiation, growth, survival, angiogenesis, and immune functions in response to signaling by extracellular cytokines and growth factors. It is also known that STAT3 protein is persistently activated through various pathways and promotes tumorigenesis. Studies on the functions of STAT3 protein in carcinogenesis and metastasis demonstrate that when excessively activated, STAT3 protein is closely related to cancer angiogenesis and metastasis. In addition to these, STAT3 is known to play a central role in the initiation, development, and progression of tumors, including cancer growth, anti-apoptosis, anticancer resistance in the invasive tumor microenvironment, and immune escape. Persistent activity of STAT3 is closely related to a broad range of human tumors. Thus, STAT3 is considered a new target for tumor prevention and therapy.

SUMMARY OF THE INVENTION

The present invention is intended to construct a platform using a nanoplasmonic biosensor based on gold nanoparticles to track the STAT3 signaling pathway and to use the platform for screening inhibitors of STAT3 phosphorylation and dimerization.

An aspect of the present invention provides a method for screening an anticancer candidate, including immobilizing gold nanoparticles onto a substrate; binding a protein involved in carcinogenesis and metastasis to the immobilized gold nanoparticles, recording a spectrum of the protein conjugate, and analyzing the spectrum to obtain reference data; adding a candidate inhibiting the activity of the protein to the protein conjugate, recording a spectrum of the mixture, and analyzing the spectrum to obtain comparative data; and comparing the reference data with the comparative data to determine whether the candidate inhibits the activity of the protein.

According to one embodiment of the present invention, the protein involved in carcinogenesis and metastasis may be selected from proteins involved in immune signaling.

According to a further embodiment of the present invention, the protein involved in carcinogenesis and metastasis may be selected from the group consisting of STAT1, STAT2, STAT3, STAT4, STAT5a, STAT5b, STAT6, and combinations thereof.

According to another embodiment of the present invention, the protein involved in carcinogenesis and metastasis may be STAT3 protein.

According to a further embodiment of the present invention, the spectra may be analyzed by measuring Rayleigh light scattering spectra of the gold nanoparticles using dark-field microspectroscopy.

According to another embodiment of the present invention, the spectra may be analyzed by measuring localized surface plasmon resonance (LSPR) $\Delta\lambda_{max}$ shifts.

According to another embodiment of the present invention, the addition of the candidate inhibiting the activity of the protein may induce changes in the phosphorylation and dimerization of the STAT3 protein and the binding profile of the STAT3 protein with the gold nanoparticles on the substrate.

According to another embodiment of the present invention, the gold nanoparticles may be amino-modified spherical gold nanoparticles.

According to another embodiment of the present invention, the amino-modified spherical gold nanoparticles may be synthesized by sodium borohydride reduction of an aqueous $HAuCl_4$ solution in the presence of 2-aminoethanethiol.

According to another embodiment of the present invention, the amino-modified spherical gold nanoparticles may be immobilized onto a glutaraldehyde coated coverslip slide as the substrate by dropping a solution of the amino-modified spherical gold nanoparticles.

The method of the present invention enables screening of a candidate inhibiting the activity of a protein involved in carcinogenesis and metastasis in an accurate and convenient manner.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 1A is a scheme of the synthesis of amino-modified gold nanoparticles, FIG. 1B shows a HR-TEM image (left) and a HR-SEM image (right) of ~50 nm spherical gold nanoparticles (AuNPs), FIG. 1C shows a dark-field image of amino-modified gold nanoparticles at a magnification of 1000×, FIG. 1D shows UV-Vis absorption spectra used to confirm the STAT3 signaling pathway (The arrows in the dashed box indicate the absorbance peak of AuNPs (black, 534 nm), STAT3 protein-AuNPs (blue, 541.5 nm) and dimerization of STAT3 protein-AuNPs (red, 543.5 nm), respectively), and FIG. 1E shows LSPR shifts at different concentrations of STAT3 protein at the single AuNP-STAT3 protein binding step;

FIG. 3A shows overall experimental processes for tracking of the STAT3 signaling pathway and inhibition of STAT3 dimerization and FIG. 3B represents the system setup using a dark-field microscope;

FIG. 4A shows LSPR shifts at different concentrations of STAT3 protein at the STAT3 dimerization step, FIG. 4B shows LSPR shifts at different concentrations of the inhibitor (STA-21) in the inhibition of STAT3 dimerization, and FIG. 4C shows LSPR shifts according to the STAT3 signaling pathway including phosphorylation, dimerization and inhibition of STAT3 dimerization using recombinant STAT3 protein and a real sample (Inset: representative Rayleigh light scattering spectra of the STAT3 signaling pathways according to the phosphorylation and dimerization using the recombinant STAT3 protein);

FIG. 5A shows the results of Native polyacrylamide gel electrophoresis (Native PAGE) of STAT3 protein and FIG. 5B shows the concentrations of STAT3 protein in MCF-7 cell lysates (STAT3 protein extracted from MCF-7 cells which were untreated STA-21 (left column) and treated with STA-21 (right column));

DETAILED DESCRIPTION OF THE INVENTION

Figure 1A:
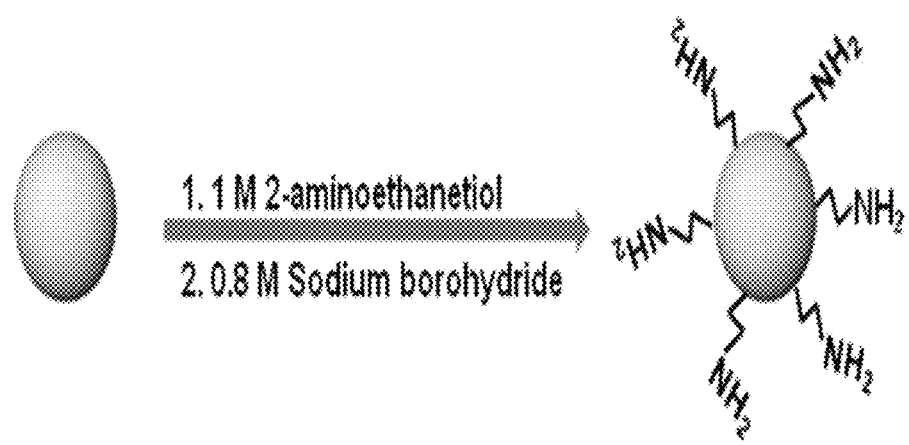
FIGS. 1A-1E explain the synthesis of gold nanoparticles, specifically.

The present invention will now be described in more detail.

The present inventors used a nanoplasmonic biosensor based on gold nanoparticles for tracking of the signaling pathway of a protein playing a key role in carcinogenesis and metastasis and succeeded in tracking the signaling pathway using a known inhibitor of the protein. Furthermore, the present inventors succeeded in tracking the signaling pathway and inhibition effects using real sample (MCF-7 cell line) by using the platform.

Thus, the present invention provides a method for screening an anticancer candidate, including immobilizing gold nanoparticles onto a substrate; binding a protein involved in carcinogenesis and metastasis to the immobilized gold nanoparticles, recording a spectrum of the protein conjugate, and analyzing the spectrum to obtain reference data; adding a candidate inhibiting the activity of the protein to the protein conjugate, recording a spectrum of the mixture, and analyzing the spectrum to obtain comparative data; and comparing the reference data with the comparative data to determine whether the candidate inhibits the activity of the protein.

In the method of the present invention, a gold nanoparticle-immobilized substrate is fabricated as a nanobiosensor and the binding profiles of the nanobiosensor with an analyte protein in the absence and presence of a specific candidate are analyzed by spectroscopy to determine whether the candidate inhibits the activity of the analyte protein.

According to the method of the present invention, first, gold nanoparticles are immobilized onto a substrate to fabricate a nanosensor onto which an analyte protein involved in carcinogenesis and metastasis can be immobilized. The gold nanoparticles are amino-modified spherical gold nanoparticles, which may be, for example, synthesized by sodium borohydride reduction of an aqueous $HAuCl_4$ solution in the presence of 2-aminoethanethiol. The amino-modified spherical gold nanoparticles may be immobilized onto a glutaraldehyde coated coverslip slide as the substrate by dropping a solution of the amino-modified spherical gold nanoparticles.

Next, a protein involved in carcinogenesis and metastasis is bound to the gold nanoparticles on the substrate. The protein is the target of an anticancer candidate in the phosphorylation or dimerization step. A spectrum of the protein conjugate is recorded and is analyzed to obtain reference data. In the Examples section that follows, STAT3 protein was used as the target protein involved in carcinogenesis and metastasis. However, any protein that can be attached to gold nanoparticles and subjected to spectroscopy after light irradiation may be applied to the method of the present invention. Examples of target proteins applicable to the method of the present invention include, but are not limited to, STAT1, STAT2, STAT3, STAT4, STAT5a, STAT5b, and STAT6. These proteins may be used alone or in any combination thereof. The reference data obtained without a candidate drug in a phosphorylation or dimerization step are provided for comparison with comparative data obtained after addition of the candidate drug in the same step.

Subsequently, a candidate inhibiting the activity of the protein is added to the protein conjugate and a spectrum of the mixture is recorded and analyzed to obtain comparative data. By comparison between the reference data the comparative data, a determination can be made as to whether the candidate has anticancer activity against the target protein.

The spectra may be analyzed by measuring Rayleigh light scattering spectra of the gold nanoparticles using dark-field microspectroscopy, particularly by measuring the localized surface plasmon resonance (LSPR) $\Delta\lambda_{max}$ shifts.

For example, the protein involved in carcinogenesis and metastasis may be STAT3 protein. In this case, the binding profile of the STAT3 protein with the gold nanoparticles on the substrate varies depending on the phosphorylation and dimerization of the STAT3 protein, which causes a change in LSPR $\Delta\lambda_{max}$ value.

The anticancer candidate screening method of the present invention is ultrasensitive and does not require additional labels, such as fluorescent compounds. In addition, by simple measurement of the LSPR $\Delta\lambda_{max}$ shift in the presence of a specific candidate, the influence of the candidate on the protein involved in carcinogenesis and metastasis can be analyzed. Thus, it is expected that the method of the present invention will be a strong means for drug screening of an anticancer candidate in an accurate and effective manner.

The present invention will be explained in more detail with reference to the following examples. However, these examples are provided to assist in understanding the invention and are not intended to limit the scope of the present invention.

1. Materials and Methods 1.1 Materials

N-Hydroxysuccinimide (NHS), N-ethyl-N-(diethylaminopropyl)carbodiimide (EDC), 2-aminoethanthiol, sodium borohydride, gold (III) chloride trihydrate (≥99.0%), glutaraldehyde solution, dimethyl sulfoxide (DMSO), recombinant human STAT3, recombinant human STAT1, Coomassie brilliant blue G solution and ColorBurst™ Electrophoresis Marker were purchased from Sigma Aldrich (Korea). Active full-length human Src protein and STAT3 (pY705) ELISA Kits were purchased from Abcam. ATP solution (100 mM) was purchased from Thermo Scientific™. STA-21 was purchased from Santa Cruz Biotechnology. Purified BSA 100× was purchased from New England Biolabs. Nuclease-free water was purchased from Promega Corporation. Coverslip slides (22×40×0.1 mm) were purchased from Deckglaser (Germany). Ultra-pure water (18.2 mΩcm$^{-1}$) was used to prepare all solutions.

1.2 Synthesis of Gold Nanoparticles

In accordance with the method described in Y. Jv, B. Li and R. Cao, Chem. Commun., 2010, 46, 80178019, amino-modified spherical gold nanoparticles (AuNPs) were synthesized by sodium borohydride reduction of an aqueous HAuCl$_4$ solution in the presence of 2-aminoethanethiol. The glass vial was cleaned with aqua regia (3:1 HNO$_3$/HCl) and rinsed with ultrapure water (18.2 mΩcm$^{-1}$). Next, 20 mL of 0.36 mM HAuCl$_4$ and 42.5 μL of 213 mM 2-aminoethanthiol were added with vigorous stirring at room temperature. After 20 min, 1.05 μL of 8 mM sodium borohydride was added and stirred vigorously for 16 h. The suspension was filtered using a 0.22 μm filter to remove any aggregated particles. UV-vis absorption spectra of the gold solution were recorded using a lifescience UV-Vis spectrophotometer (DUR 730, Beckman). The size and morphology of the synthesized AuNPs were estimated by high-resolution transmission electron microscopy (HRTEM, JEOL JEM-3011 operated at 300 kV).

1.3 Fabrication of Single Nanoplasmonic Biosensor

Figure 2:
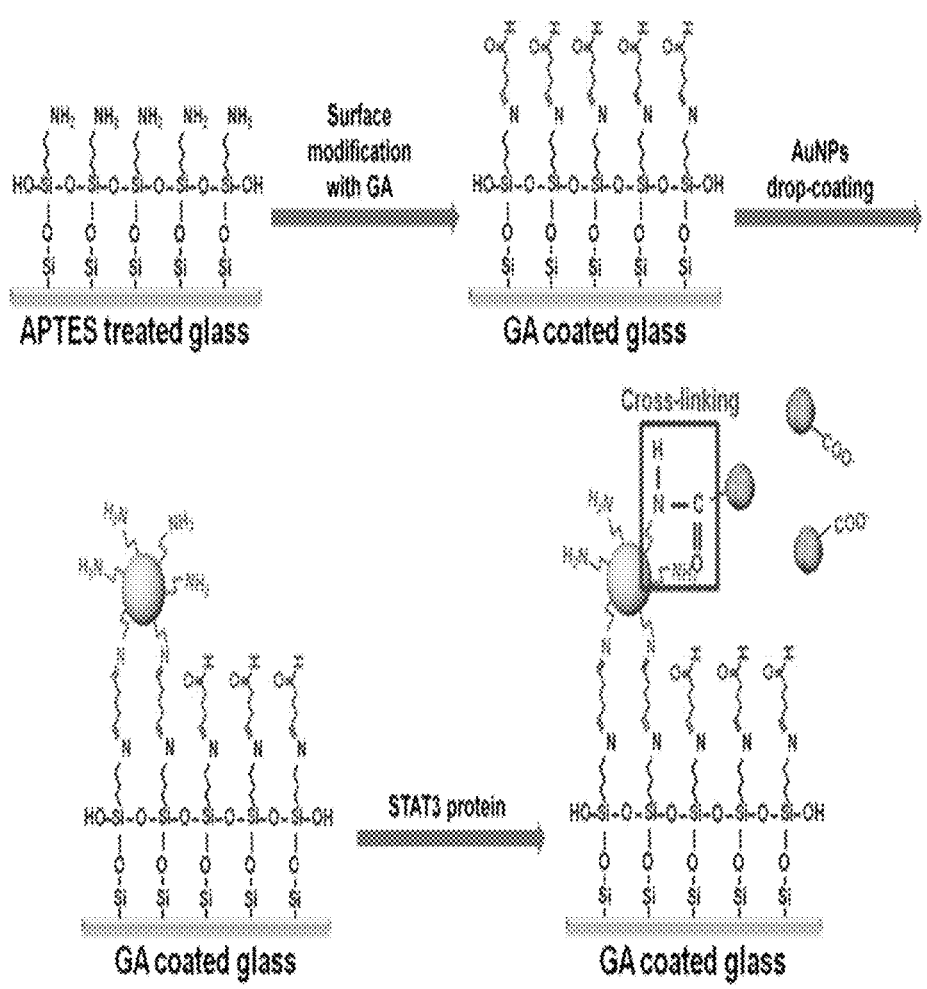
FIG. 2 shows overall mechanisms for amino-modified gold nanoparticle immobilization onto a glutaraldehyde coated coverslip slide and subsequent conjugation with STAT3 protein.

Individual amino-modified AuNPs, ~50 nm AuNPs, were immobilized onto a glutaraldehyde coated coverslip slide (22×40×0.1 mm) by dropping 10 μL of the dilute amino-modified AuNP solution (FIG. 2). The glass slide was mounted to an RC-30HV closed-bath imaging chamber (Warner Instruments, USA) to visualize the AuNPs after the addition of adsorbates and reactants. The imaging chamber (Warner Instruments, USA) was subsequently inserted onto the holder of the darkfield microscope (Eclipse TE2000-U, Nikon, Japan), and the fluidic flow was set at 100 μL min$^{-1}$ by connection to a syringe pump (Harvard Apparatus).

Figure 3A:
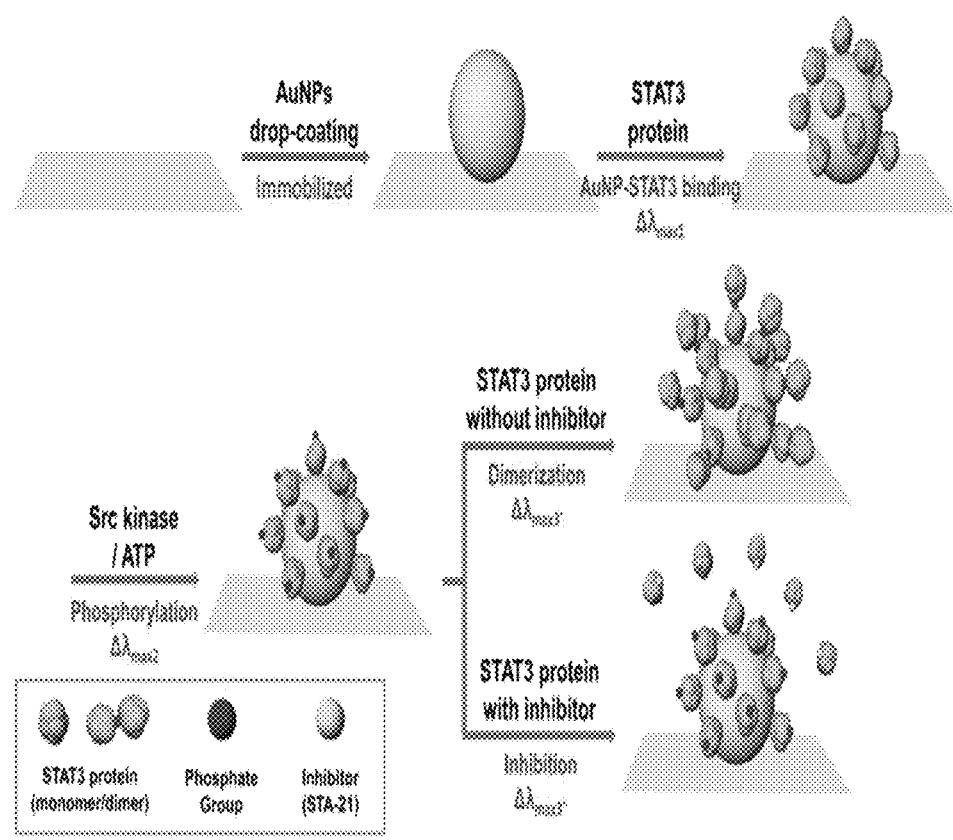
FIGS. 3A and 3B schematically explain the fabrication of a single nanoplasmonic biosensor, specifically.
Figure 7:
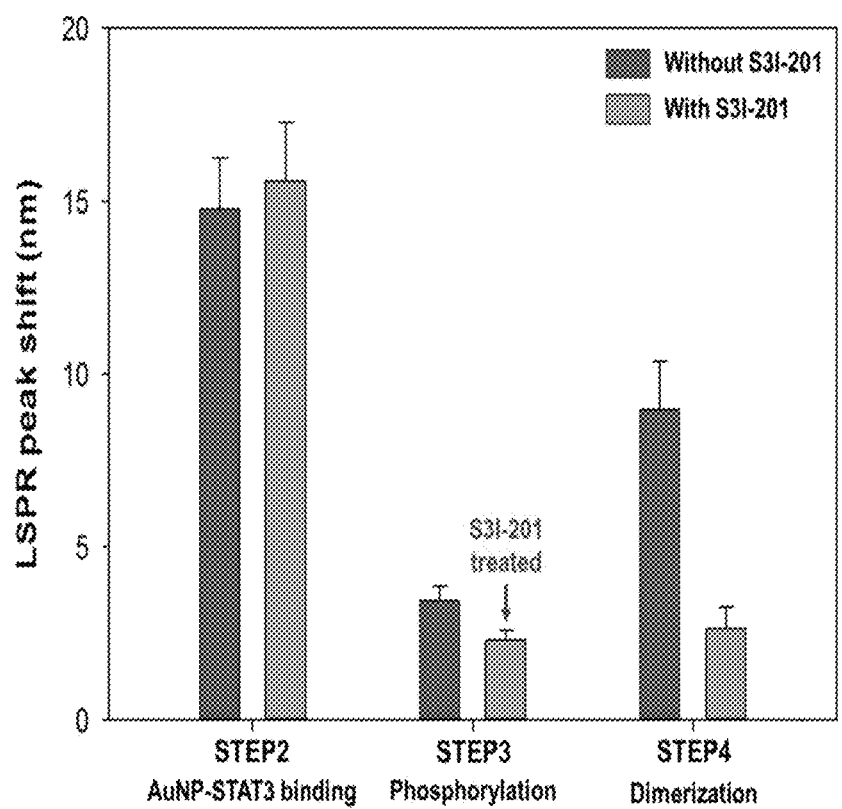
FIG. 7 shows LSPR shifts according to the STAT3 signaling pathway including phosphorylation, dimerization, and inhibition of STAT3 phosphorylation using recombinant STAT3 protein.

Subsequently, the phosphorylation and the dimerization of STAT3 were conducted as follows. In the first step, after ~50 nm AuNPs were immobilized onto a coverslip slide, all unbound AuNPs and contaminants were removed, and the surface of the amino-modified AuNPs was cleaned by injecting nuclease-free water for 1 h. In the second step, after STAT3 protein was conjugated to the AuNPs, 300 μL of the STAT3 solution (10 μmL$^{-1}$ in 50 mM Tris-HCl buffer, pH 7.4, containing 150 mM NaCl and 25% glycerol) containing STAT3 protein (10 μg mL$^{-1}$) was injected into the immobilized AuNPs and incubated overnight. In the third step, the kinase reaction, 300 μL of Src kinase (1 ng mL$^{-1}$) and ATP solution (200 μM) were injected into the imaging chamber and incubated for 2 h. In the fourth step, the STAT3 dimerization, Tris-HCl buffer (pH 7.4) containing STAT3 protein (10 μg mL$^{-1}$), Src kinase (1 ng mL$^{-1}$) and ATP solution (200 μM) was injected into the imaging chamber and incubated for 8 h. To assay the inhibitory effect on the phosphorylation of the STAT3 protein, the third step was performed in the presence of S31-201 (1 μM) which is a small molecule inhibitor of STAT3 protein phosphorylation (FIG. 7). To assay the inhibitory effect on the dimerization of the STAT3 protein, the fourth step was performed in the presence of STA-21 (1 μM) which is a small molecule inhibitor of STAT3 protein dimerization (FIG. 3A).

Phosphorylated STAT3 protein (10 μg mL$^{-1}$) extracted from Michigan Cancer Foundation-7 (MCF-7) cells was used to evaluate the performance of the biosensor instead of the recombinant STAT3 protein used in the dimerization and inhibition of dimerization.

To validate the unspecific binding on the nanosensor surface, three control experiments were conducted independently from each other. In control 1, BSA was used in step 2 instead of recombinant STAT3 protein. In control 2, no ATP was used in step 3. In control 3, the phosphorylated STAT1 (Tris-HCl buffer (pH 7.4) containing STAT1 protein (10 μg mL$^{-1}$), Src kinase (2 μg mL$^{-1}$) and ATP solution (200 μM) was used instead of phosphorylated STAT3.

The changes in the LSPR spectra of the single amino-modified AuNPs in response to STAT3 protein conjugation, STAT3 phosphorylation, dimerization or inhibition of STAT3 dimerization were recorded. To determine $\lambda_{max}$, the Lorentzian algorithm was applied to the experimental spectrum using OriginPro 8 software. The wavelength shift ($\Delta\lambda_{max}$) was calculated using the following formula: $\lambda_{max}$ (after reaction)−$\lambda_{max}$ (before reaction).

1.4 Biochemical Assay 1.4.1 Native Polyacrylamide Gel Electrophoresis (PAGE)

Analysis of STAT3 dimerization and inhibition of STAT3 dimerization was confirmed by native polyacrylamide gel electrophoresis on 6% native gels using a standard protocol (Y. Jv, B. Li and R. Cao, Chem. Commun., 2010, 46, 80178019). The samples which formed the dimerization and inhibited the dimerization were loaded into the 6% native gel running at a voltage of 10 V cm$^{-1}$.

1.4.2 Enzyme-Linked Immunospecific Assay (ELISA)

To measure the concentration of STAT3 protein in MCF-7 cell lysates, 50 μL of MCF-7 samples or standards and an antibody cocktail were incubated in each well for 1 h at room temperature with gentle shaking. The solution was then discarded, and the wells were washed 3 times with buffer. A 100 μL aliquot of the TMB one-step substrate reagent was added to each well and incubated for 15 min in the dark on a plate shaker at 400 rpm. Finally, 100 μL of stop solution was added to each well, and the absorbance at 450 nm was measured immediately (Shimadzu UV3600 UV-vis-NIR).

1.5 Cell Culture

The MCF-7 cells, human breast tumor cell lines, were cultured in Dulbecco's modified Eagle's medium (DMEM, Thermo Scientific, USA) containing 10% (v/v) fetal bovine serum (FBS, Thermo Scientific, USA) and 3% penicillin/streptomycin (Thermo Scientific, USA) at 37° C. in a humidified atmosphere containing 5% CO$_2$. The inocula of cells were determined using a hemacytometer with a vital dye, trypan blue. Also, in the sample preparation for blocking the STAT3 signaling pathway, MCF-7 cells were treated with STA-21 (inhibitor of STAT3 dimerization) and incubated for 24 h. Then cells were lysed in cold RIPA lysis buffer containing protease inhibitors and subjected to experiments.

2. Results and Discussion 2.1 Sensor Fabrication

Figure 1B:
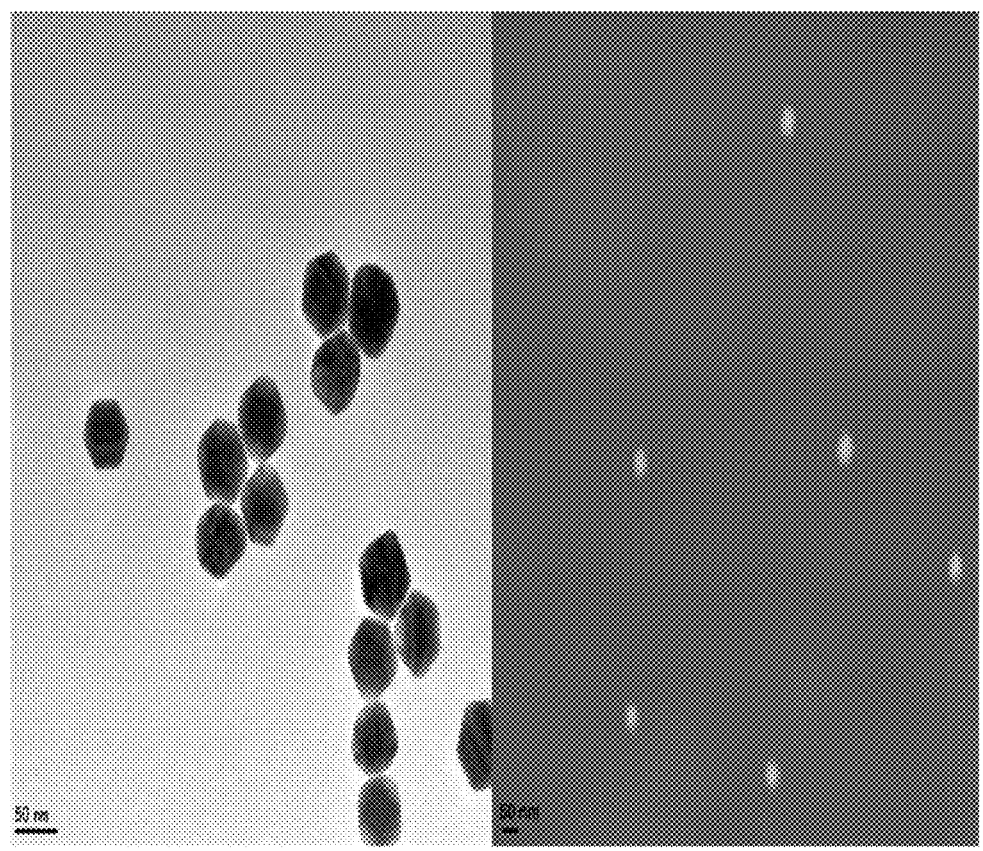
Figure 1C:
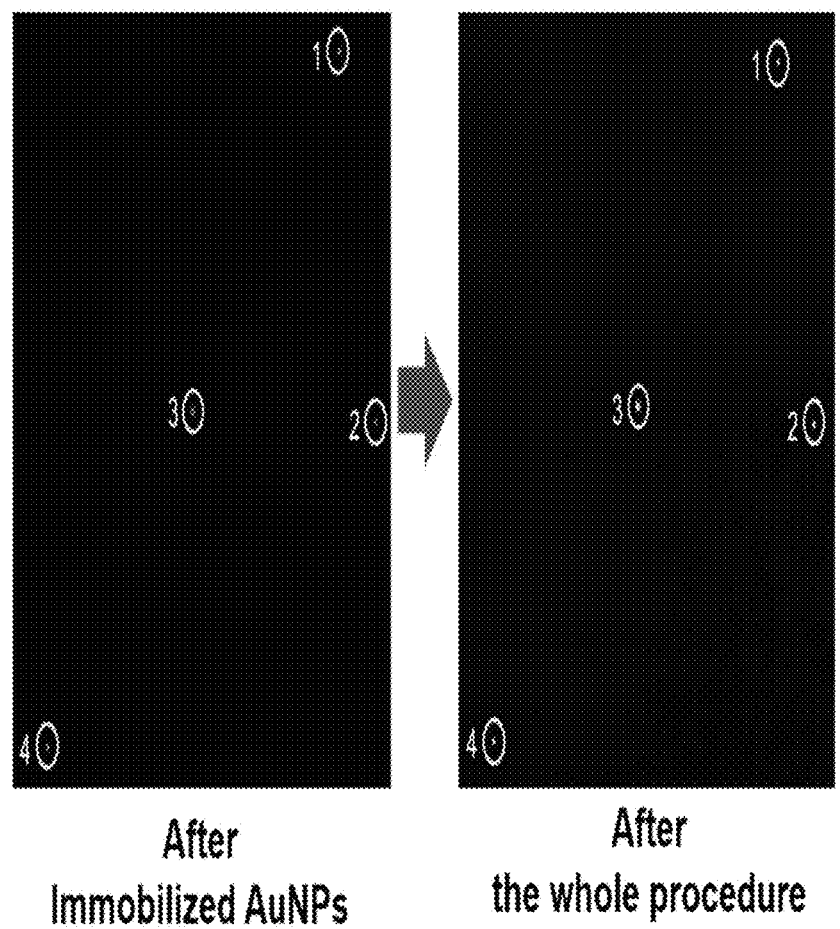
Figure 1D:
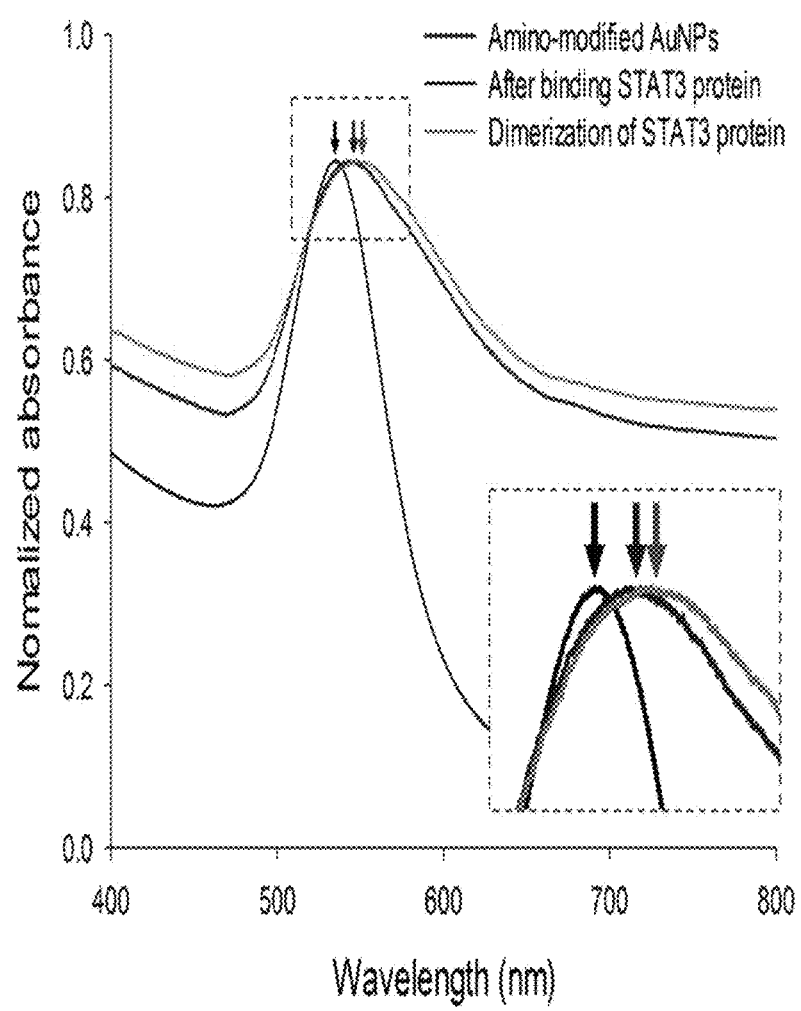

For fabrication of the sensor, the amino-modified AuNPs (~50 nm) were synthesized (FIG. 1A) and estimated using HR-TEM/SEM images (FIG. 1B), dark-field images (FIG. 1C) and UV-VIS spectroscopy (FIG. 1D). In the present invention, the amino-modified AuNPs were synthesized with 2-aminoethanethiol which is well-known chemical used as a reducing and stabilizing agent. It is also used as a linking agent for STAT3 protein conjugation. The thiol group (SH) of 2-aminoethanethiol bound to the surface of the AuNPs, and the amino group (NH$_2$) of 2-aminoethanethiol remained exposed on the surface. The amino-modified AuNPs were immobilized onto a glutaraldehyde coated coverslip slide by covalent bonds (FIG. 2). After AuNPs were immobilized onto a coverslip slide, the phosphorylation and dimerization of STAT3 protein were tracked. These reactions occurred on the surface of the single AuNPs. In this example, the ~50 nm AuNPs were selected using the dark-field image (FIG. 1C) and the same particle was monitored in each step. As shown in FIG. 1C, after the whole procedure, the amino-modified AuNPs were immobilized and kept the same position on the coverslip slide. Also, in this example, the STAT3 protein monomers where the carboxyl group ($CO_2H$) had been activated by NHS/EDC were added. The activated carboxyl group ($CO_2$—) of STAT3 covalently bound with the amino group ($NH_2$) of the AuNPs (FIG. 2).

FIG. 1D shows the UV-VIS spectrum of the STAT3 signaling pathway on amino-modified AuNPs. Because of the plasmon resonance characteristic of AuNPs, the damping of the surface plasmon band compared with the amino-modified AuNPs was observed as a red-shift of 7.5 nm and 9.5 nm, corresponding to binding with STAT3 protein monomers and dimerization of STAT3 protein, respectively. This result indicates that amino-modified AuNPs were conjugated to the STAT3 monomers and successfully induced the phosphorylation and dimerization of the STAT3 protein.

Figure 1E:
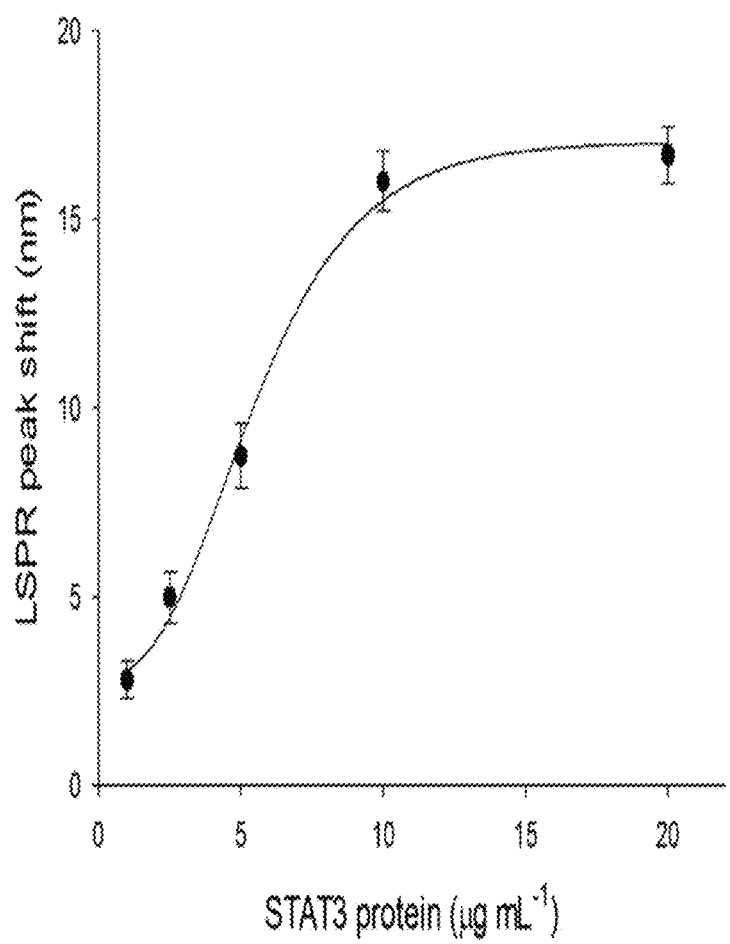

Subsequently, the optimal concentration of the STAT3 monomer for conjugation on the surface of single amino-modified AuNPs was determined. In this example, the concentration range of the STAT3 monomers was varied from 1 μg $mL^{-1}$ to 20 μg $mL^{-1}$. As shown in FIG. 1E, the red shift of the LSPR maximum wavelength (LSPR $\Delta\lambda_{max}$) based on the concentration of the recombinant STAT3 monomer increased from 1 μg $mL^{-1}$ to 10 μg $mL^{-1}$ and saturated at 10 μg $mL^{-1}$. Therefore, in this example, the optimal STAT3 monomer concentration was selected at 10 μg $mL^{-1}$ which is appropriate for tracking of the phosphorylation and dimerization of STAT3 protein, because all the amino groups on single AuNPs were conjugated by the recombinant STAT3 monomer.

2.2 Tracking of Phosphorylation and Dimerization of STAT3 Protein

Figure 3B:
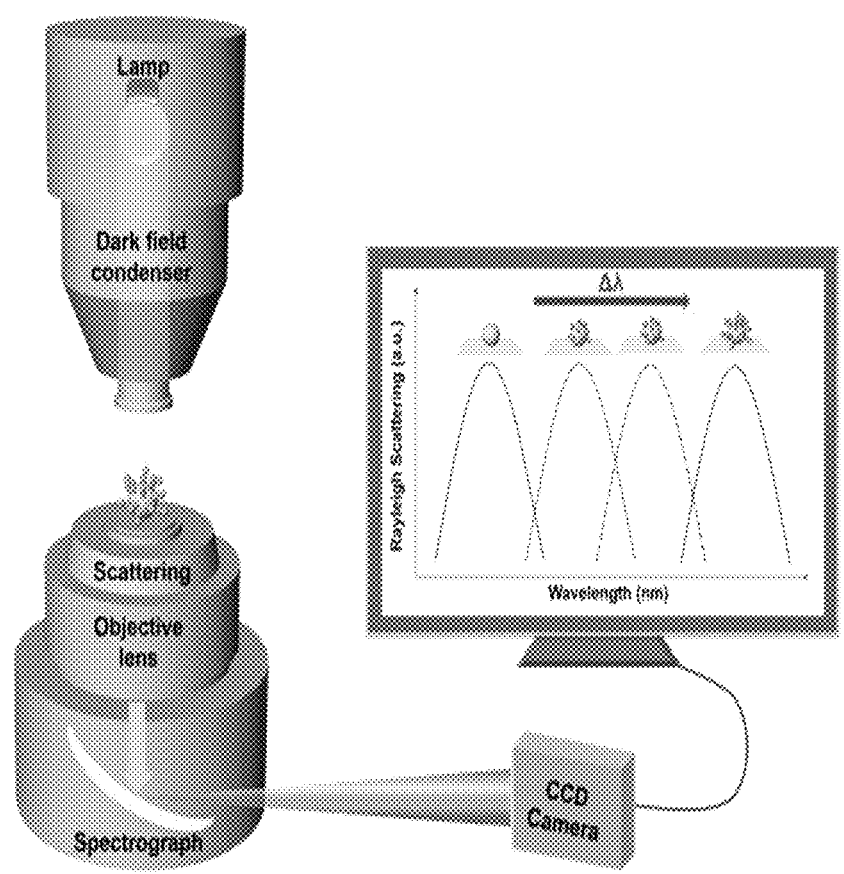

As shown in FIG. 3A, the surface of the single amino-modified AuNPs is first conjugated with the STAT3 protein monomers (10 μg $mL^{-1}$), which has a molecular weight of 90 kDa, including the SRC homology 2 (SH2) domain and tyrosine phosphorylation residue (Y705). The STAT3 monomers are then phosphorylated at a specific tyrosine residue (Y705) by Src kinase (1 ng $mL^{-1}$) and the adenosine triphosphate (ATP) solution (200 μM). Subsequently, phosphorylated STAT3 proteins form homo-dimers through reciprocal phosphotyrosine (pY705)-SH2 domain interactions between the STAT3 monomers. The phosphorylation and dimerization of STAT3 were tracked by the Rayleigh light scattering spectra using dark-field microspectroscopy (FIG. 3B). In the beginning of the measurement step, the spectrum of the background was normalized to zero at an area near the individual AuNP.

Figure 4A:
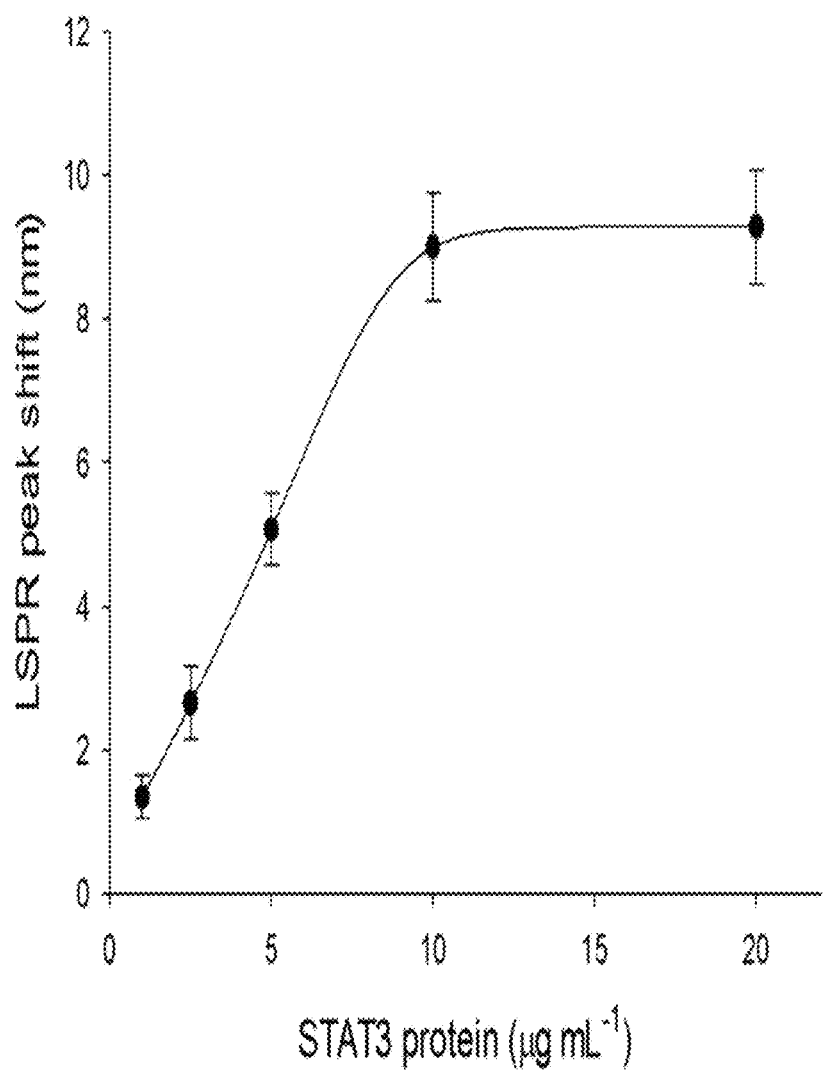
FIGS. 4A-4C show tracking of the STAT3 signaling pathway and inhibition of STAT3 dimerization on the nanosensor surface, specifically.

FIG. 4A shows the LSPR shifts at the dimerization step which increased according to the concentration of STAT3 protein. In this example, various concentrations of STAT3 protein from 1 μg $mL^{-1}$ to 20 μg $mL^{-1}$ were investigated. When the STAT3 protein concentration is 10 μg $mL^{-1}$, a red shift of the LSPR $\lambda_{max}$ for the dimerization step was recorded as 9.00 nm. Therefore, the optimal concentration of STAT3 protein at the dimerization step was determined to be 10 μg $mL^{-1}$.

Figure 4B:
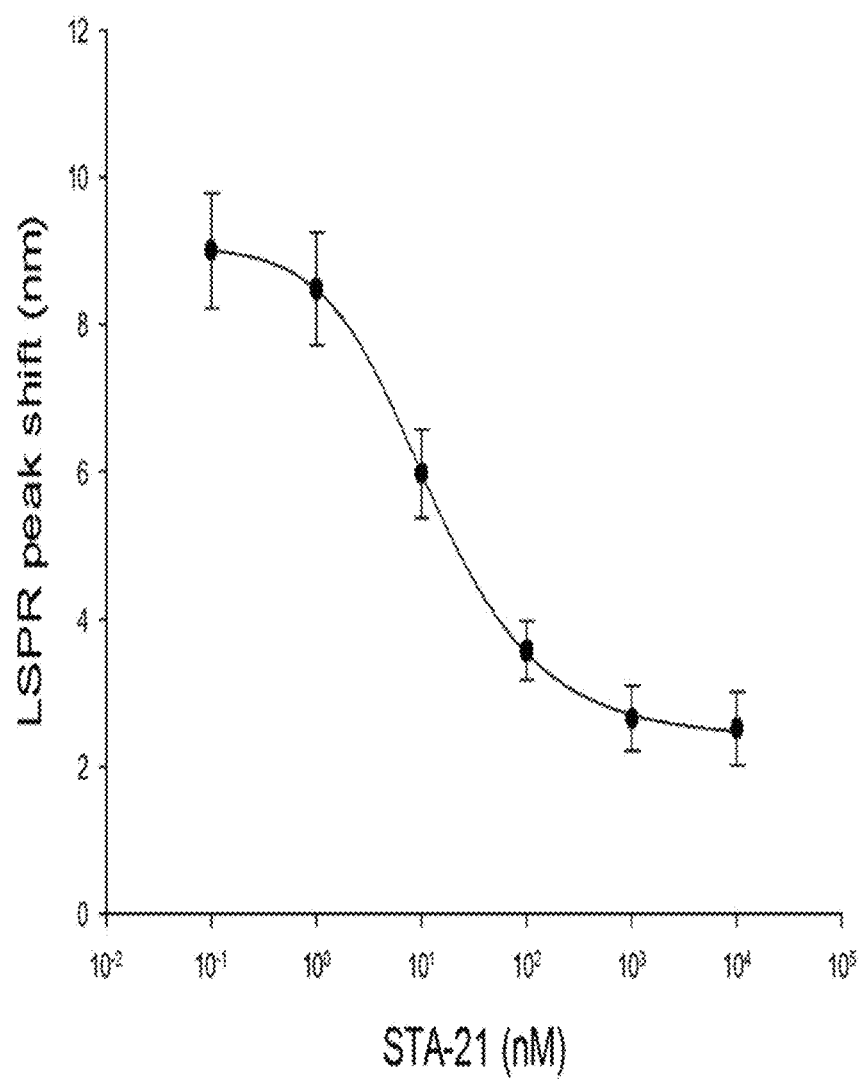
Figure 4C:
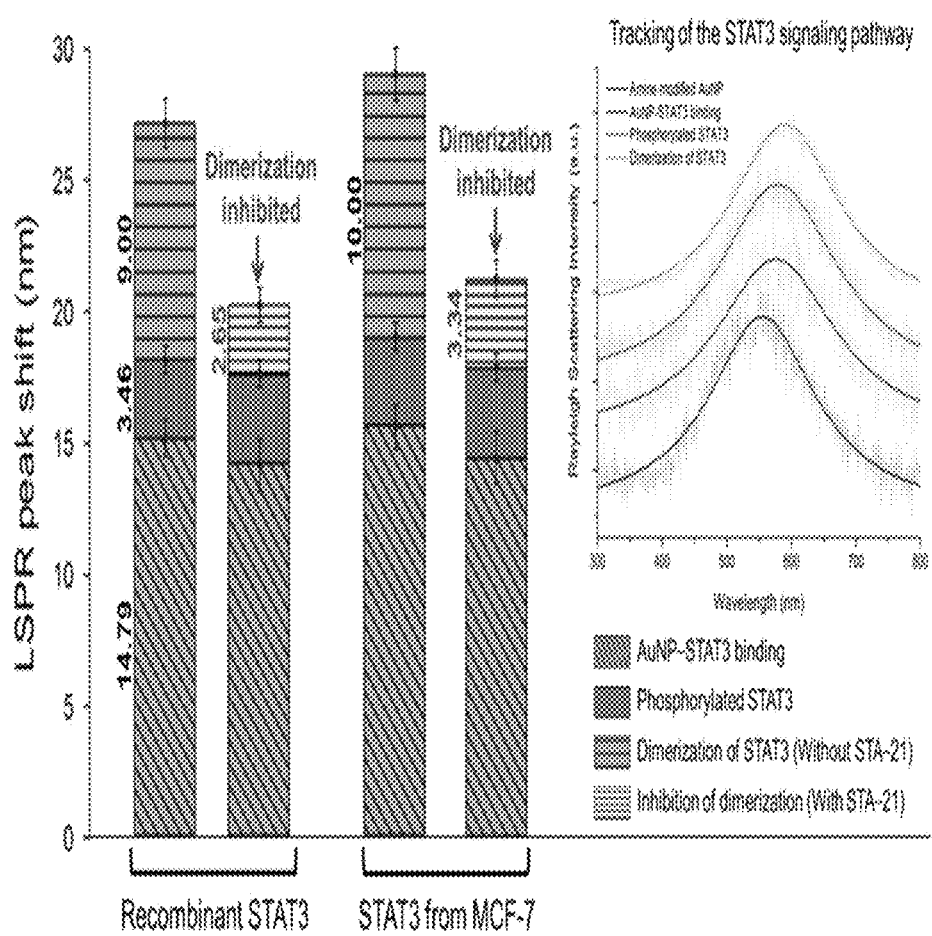

As shown in FIG. 4C (recombinant STAT3 protein) and the inset, tracking of phosphorylation and dimerization of STAT3 revealed a red shift of the LSPR maximum wavelength (LSPR $\Delta\lambda_{max}$) of 14.79 nm, 3.46 nm and 9.00 nm for STAT3 monomer bioconjugation on the single amino-modified AuNP, phosphorylation, and dimerization of STAT3 protein, respectively. These significant LSPR peak shifts indicate binding events of the phosphorylation and dimerization of STAT3 on the single AuNP surface which induces the change of the refractive index on AuNPs.

2.3 Inhibition of STAT3 Dimerization on the Nanosensor Surface

After the successful tracking of the STAT3 signaling pathway, an attempt was made to monitor the inhibition of STAT3 dimerization using the nanosensor. Inhibition of STAT3 dimerization was performed in the presence of the inhibitor STA-21 (1 μM). STA-21 is a selective small molecule inhibitor of STAT3 protein. STA-21 binds to the SH2 domain of STAT3 protein and inhibits STAT3 dimerization, DNA binding and nuclear translocation (K. Miyoshi, M. Takaishi, K. Nakajima, M. Ikeda, T. Kanda, M. Tarutani, T. Liyama, N. Asao, J. Digiovanni and S. Sano, J. Invest. Dermatol., 2011, 131, 108-117). Therefore, STA-21 induces apoptosis in human breast tumor cell lines, also, where STAT3 is phosphorylated.

To ascertain inhibition of the STAT3 dimer, a range of STA-21 ($10^{-1}$ nM to $10^4$ nM) was applied. FIG. 4B shows that the LSPR $\Delta\lambda_{max}$ values decreased from 8.96 nm to 2.65 nm according to the concentration of STA-21. The increased concentration of STA-21 reduced the density of the STAT3 dimer formed on the surface, indicating the optimal concentration of STA-21 at $10^3$ nM, because 100% of STAT3 dimerization was inhibited by STA-21.

To ascertain the inhibition effects, the red shift of the LSPR $\lambda_{max}$ in the assay of dimerization inhibition was compared to that without inhibition. FIG. 4C (recombinant STAT3 protein) shows the red shift of the LSPR $\lambda_{max}$ was measured as 9.00 nm and 2.65 nm corresponding to the absence and presence of STA-21 in the dimerization step, respectively. STAT3 proteins on the nanosensor surface may work in similar patterns with cellular receptors such that interaction events might be affected by small molecule activity.

Figure 5A:
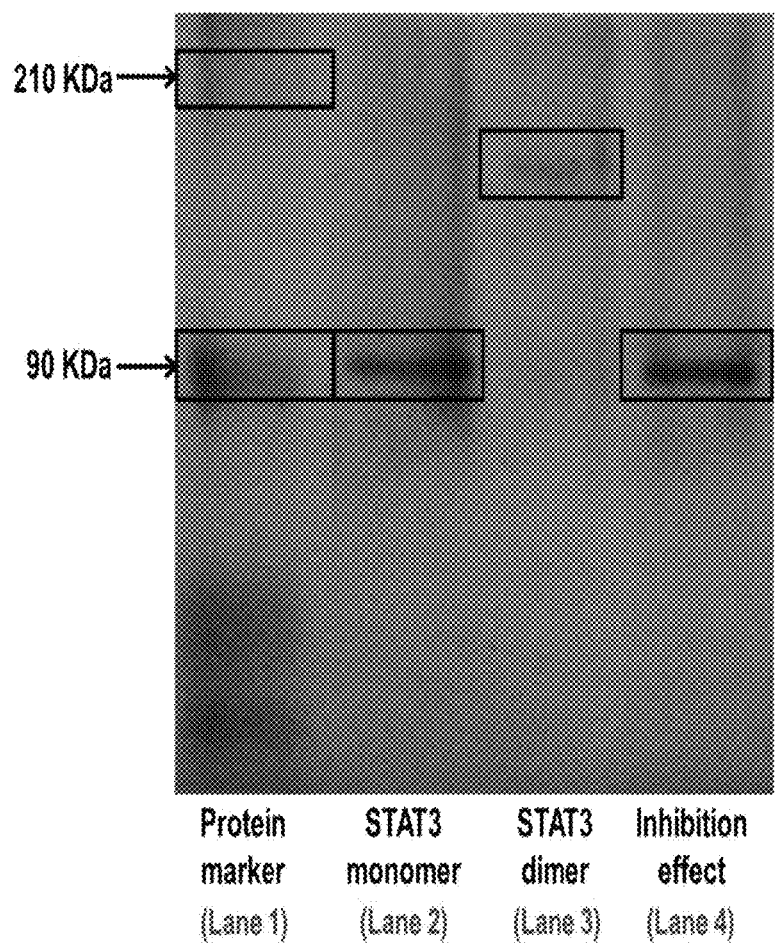
FIGS. 5A and 5B show the results of biochemical assay, specifically.

Also, Native PAGE, a typical protein binding assay, was used to measure the dimerization and inhibition of STAT3. The results (FIG. 5A) were observed with a 167 kDa STAT3 dimer (lane 3), 90 kDa monomer due to the STA-21 inhibitor (lane 4) and a 90 kDa monomer as the control (lane 2). The dimer formation was clarified by the interactions between reciprocal phosphotyrosine (pY705) and the SH2 domain of phosphorylated STAT3 protein monomers.

2.4 STAT3 Dimerization and Inhibition of STAT3 Dimerization on the Nanosensor Surface Using a Real Sample To validate that the inventive system is also compatible with real samples, STAT3 protein extracted from the Michigan Cancer Foundation-7 (MCF-7) cell line which is a well-known human breast cancer cell line was used instead of the recombinant STAT3 protein. The amino groups on single gold nanoparticles were already conjugated with phosphorylated recombinant STAT3 and they formed the STAT3 dimer with phosphorylated STAT3 from MCF-7 cells. Therefore, phosphorylated STAT3 (MCF-7) affected STAT3 dimerization, while, the STAT3 dimer did not affect the assay.

Figure 5B:
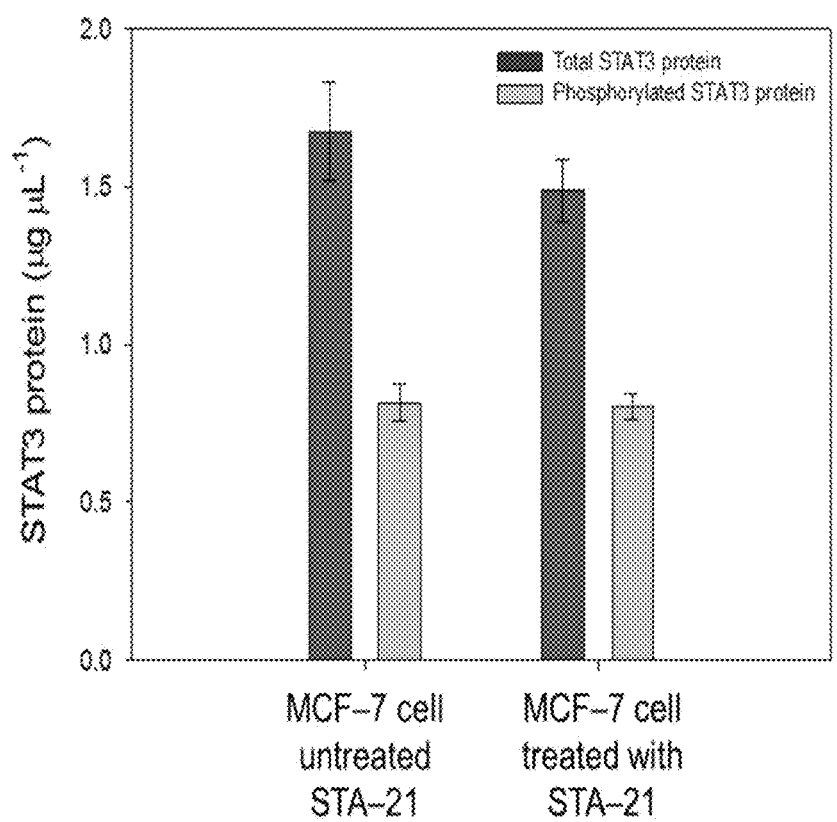

The concentration of phosphorylated STAT3 protein from MCF-7 cells was measured by ELISA (FIG. 5B) and the concentration was quantified as 10 μg mL$^{-1}$ which was the same concentration of recombinant STAT3 protein. To confirm STAT3 dimerization, the dimerization step was performed with MCF-7 cells which were not treated with STA-21. Also, to ascertain the inhibition effects, an assay of dimerization inhibition was performed with the MCF-7 cells which were treated with STA-21. The SH2 domain of STAT3 protein that was treated with the inhibitor did not form a STAT3 dimer.

As shown in FIG. 4C (STAT3 from MCF-7), the red shift of the LSPR $\lambda_{max}$ for the dimerization step was measured as 10.00 nm (in the absence of STA-21) and 3.34 nm (in the presence of STA-21), respectively. The LSPR $\Delta\lambda_{max}$ of the real sample is 1 nm higher than that using recombinant STAT3 (9.00 nm), which could be generated by hetero-dimerization with STAT1 and other unspecific binding. Moreover, activity of STA-21 could be shared in the inhibition of other dimerization molecules which are present in the cell extract, which results in a higher density of STAT3 dimerization on the nanosensor surface. However, the different LSPR $\Delta\lambda_{max}$ between real (3.34 nm) and recombinant STAT3 protein (2.65 nm) is 0.69 nm. That is insignificant because it is smaller than the standard deviation.

2.5 Unspecific Binding Assay

Unspecific binding of each event was carefully considered to avoid noise signals that generate artifact results. Bovine serum albumin (BSA, 10 μg mL$^{-1}$), a general blocker for protein sensors, was first used to block unspecific sites on the amino-modified AuNPs to make a pure nanosensor (black column of control 1, FIG. 6).

Since some studies have reported that unphosphorylated STAT3 can also dimerize and promote transcription (J. Yang, X. Liao, M. K. Agarwal, L. Barnes, P. E. Auron and G. R. Stark, Genes Dev., 2007, 21, 1396-1408), the dimerization of STAT3 was then measured under a condition of the unphosphorylated STAT3 monomers. The red shift of the LSPR $\lambda_{max}$ was collected at 1.53 nm (blue column of control 2, FIG. 6), which indicates the dimer forms of unphosphorylated STAT3 do not form under the experimental conditions presented here.

Figure 6:
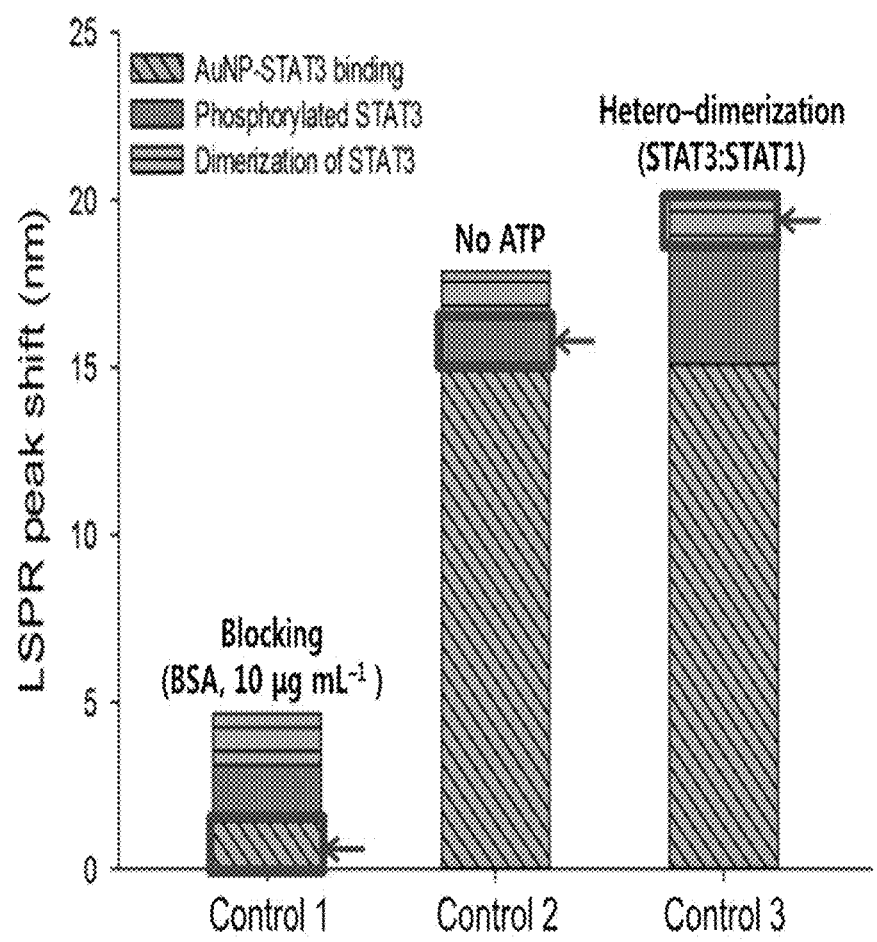
FIG. 6 shows the results of unspecific assay for phosphorylation and dimerization of STAT3 protein.

Another bias result is the hetero-dimers of STAT3 protein with other STAT family proteins because STAT3 protein is known for forming hetero-dimers with other STAT family proteins, such as STAT1 protein. Recombinant STAT1 protein (10 μg mL$^{-1}$) was injected instead of recombinant STAT3 protein for dimerization. As shown in FIG. 6 (red column of control 3), however, the LSPR maximum wavelength was slightly shifted by 1.63 nm. The slight shift was due to no formation of STAT3:STAT1 hetero-dimerization on the surface sensor. This is because the STAT3:STAT1 hetero-dimer has a lower binding affinity than the STAT3 homo-dimer. Therefore, it was found that the unspecific binding due to heterodimerization was negligible and thus the system of the present invention is suitable for verifying the formation of dimer-complexes in vitro and the inhibitory effect on the dimer-complex formation.

What is claimed is:

1. A method for screening an anticancer candidate, comprising:
    immobilizing gold nanoparticles onto a substrate;
    forming a STAT3 protein conjugate by binding a STAT3 protein involved in carcinogenesis and metastasis to the immobilized gold nanoparticles, recording a spectrum of the protein conjugate as the STAT3 protein is undergoing a phosphorylation or a dimerization step without the presence of the candidate, and analyzing the spectrum of the STAT3 protein conjugate to obtain reference data;
    forming a mixture by adding a candidate inhibiting the activity of the STAT3 protein to the STAT3 protein conjugate, recording a spectrum of the mixture as the STAT3 protein is undergoing a phosphorylation or a dimerization, and analyzing the spectrum of the mixture to obtain comparative data; and
    comparing the reference data with the comparative data to determine whether the candidate inhibits the activity of the protein,
    wherein the addition of the candidate inhibiting the activity of the protein induces changes in the phosphorylation and dimerization of the STAT3 protein and the binding profile of the STAT3 protein with the gold nanoparticles on the substrate.

2. The method according to claim 1, wherein the protein involved in carcinogenesis and metastasis is selected from proteins involved in immune signaling.

3. The method according to claim 1, wherein the spectra are analyzed by measuring Rayleigh light scattering spectra of the gold nanoparticles using dark-field microspectroscopy.

4. The method according to claim 1, wherein the spectra are analyzed by measuring localized surface plasmon resonance (LSPR) $\Delta\lambda_{max}$ shifts.

5. The method according to claim 1, wherein the gold nanoparticles are amino-modified spherical gold nanoparticles.

* * * * *